US008680107B2

(12) United States Patent
Laiho et al.

(10) Patent No.: US 8,680,107 B2
(45) Date of Patent: Mar. 25, 2014

(54) ACTIVATORS AND THERAPEUTIC APPLICATIONS THEREOF

(75) Inventors: Marikki Laiho, Kaunlalnen (FI); Karita Peltonen, Vantaa (FI)

(73) Assignee: The Johns Hopkins University, Baltimore, MD (US)

( * ) Notice: Subject to any disclaimer, the term of this patent is extended or adjusted under 35 U.S.C. 154(b) by 96 days.

(21) Appl. No.: 12/665,473

(22) PCT Filed: Jun. 19, 2008

(86) PCT No.: PCT/FI2008/050381
§ 371 (c)(1),
(2), (4) Date: Mar. 1, 2010

(87) PCT Pub. No.: WO2008/155468
PCT Pub. Date: Dec. 24, 2008

(65) Prior Publication Data
US 2010/0179155 A1   Jul. 15, 2010

(30) Foreign Application Priority Data

Jun. 20, 2007   (WO) ................. PCT/FI2007/000175

(51) Int. Cl.
| C07D 239/70 | (2006.01) |
| C07D 471/00 | (2006.01) |
| C07D 487/00 | (2006.01) |
| C07D 471/04 | (2006.01) |
| C07D 471/22 | (2006.01) |
| C07D 487/04 | (2006.01) |
| A01N 43/54 | (2006.01) |
| A61K 31/515 | (2006.01) |
| A01N 43/42 | (2006.01) |
| A61K 31/44 | (2006.01) |

(52) U.S. Cl.
USPC ........... 514/257; 514/270; 514/287; 514/626; 544/246

(58) Field of Classification Search
None
See application file for complete search history.

(56) References Cited

U.S. PATENT DOCUMENTS 5,908,840 A * 6/1999 Trova et al. ............... 514/210.21
2004/0259867 A1 * 12/2004 Fotouhi et al. ............. 514/227.5

FOREIGN PATENT DOCUMENTS

| WO | WO-00/32175 A2 | 6/2000 |
| WO | WO-02/14321 A1 | 2/2002 |
| WO | WO-2005007672 A2 | 1/2005 |
| WO | WO-2006/093518 A2 | 9/2006 |
| WO | WO-2006121767 A2 | 11/2006 |
| WO | WO-2007/107543 A1 | 9/2007 |

OTHER PUBLICATIONS

Fan et al. Bioorg.Med.Chem.Lett., vol. 7, issue 24, pp. 3107-3112.*
Fan et al., Bioorg. Med. Chem. Lett., 1997, vol. 7, No. 24, pp. 3107-3112.*
Vassilev, L.T. et al., "In vivo activation of the p53 pathway by small-molecule antagonists of MDM2", Science, 2004, vol. 303, pp. 844-848.
Ding, K. et al., "Structure-based design of potent non-peptide MDM2 inhibitors", J. Am. Chem. Soc., 2005, vol. 127, 10130-10131.
Lu, Y., "Discovery of nanomolar inhibitor of the human murine double minute 2 (MDM2)-p53 interaction through an integrated, virtual database screening strategy", J. Med. Chem., Published on Web May 26, 2006, vol. 49, pp. 3759-3762.
Deng, J. et al., "Patented small molecule inhibitors of p53-MDM2 interaction", Expert Opin. Ther. Patents, Published Feb. 1, 2006, vol. 16, pp. 165-188.
Vassilev, L.T., "MDM2 inhibitors for cancer therapy", Trends in Molecular Medicine, 2007, vol. 13, pp. 23-31.
Wilson et al., "Synthesis of 5-deazaflavin derivatives and their activation of p53 in cells," Bioorganic & Medicinal Chemistry, Nov. 15, 2000, vol. 15, No. 1, pp. 77-86.
Fotouhi, Nader et al., "Small Molecule inhibitors of p53/MDM2 interaction," Current Topics in Medicinal Chemistry, Apr. 1, 2005, vol. 5, No. 2, pp. 159-165.
Peltonen, Karita at al., "Identification of novel p53 pathway activating small-molecule compounds reveals unexpected similarities with known therapeutic agents," PLOS One, Public Library of Science, US, Jan. 1, 2010, vol. 5, No. 9, pp. E12996.

* cited by examiner

*Primary Examiner* — James D Anderson
*Assistant Examiner* — Stephanie Springer
(74) *Attorney, Agent, or Firm* — Johns Hopkins Technology Transfer

(57) ABSTRACT

The invention presents methods of identifying small molecule compounds that are activators of tumor suppressor protein p53 pathway, and its associated family members p63 and p73, function. The invention is further drawn to methods of killing tumor cells and treating cancers or other conditions requiring activation of the p53 family member pathways and DNA damage response pathways with the small molecules.

4 Claims, 8 Drawing Sheets

ACTIVATORS AND THERAPEUTIC APPLICATIONS THEREOF

This Application is the National Phase Under 35 U.S.C. §371 of PCT International Application No. PCT/FI2008/050381 which has an International filing date of Jun. 19, 2008, which claims priority to Finnish Application No. PCT/FI2007/000175 filed on Jun. 20, 2007. The entire contents of all applications listed above are hereby incorporated by reference.

FIELD OF THE INVENTION

The present invention describes methods identifying small molecules, which activate the tumor suppressor p53 pathway and/or members of the p53 protein family. The present invention is further directed to methods of activating the tumor suppressor p53 pathway, or its associated family members, p63 and p73 proteins (hereafter collectively termed as the p53 or p53 pathway) by the small molecule compounds and methods of treating cancer and diseases that require the manipulation of p53 pathway activity with the small molecules. This pathway activation may include pathways acting upstream of p53, like the DNA damage response, enzymes modifying p53, and downstream, namely through p53 family activated events. More specifically, the invention relates to compounds which can induce p53 pathway activity, and which can be used therapeutically, either alone or in combination with another therapy. The therapeutic usage includes diseases such as cancer as well as other conditions where the activation of the p53 pathway response is beneficial.

BACKGROUND OF THE INVENTION

The tumor suppressor p53 plays a central role in a process by which a cell senses and responds to a variety of stresses. It acts as a critical monitor preventing the survival of cells with genetic, and possibly, other types of permanent damage which are beyond repair. These responses prevent the accumulation of damaged and transformed cells and protect the organisms from processes that could lead to malignant formation. The key properties of p53 clearly indicate its importance in the cellular stress and damage responses of the cells. The levels of p53 are tightly regulated in normal unstressed cells by the MDM2 gene product, which binds p53 and targets p53 for ubiquitin-mediated degradation by the proteasome. DNA-damaging agents (e.g. ionising or non-ionizing radiation and cytotoxic drugs) and other types of stresses (e.g. hypoxia and oncogenes) activate p53 leading to activation of the p53 transcriptional program. This includes transactivation of a vast number of the p53 downstream target genes such as $p21^{WAF1/CIP1}$ (p21) and a number of apoptosis associated targets (e.g. PUMA, NOXA, PIGs etc.), many of which are yet to be characterized (Zhao et al, 2000; Wang et al, 2001; Wei et al., 2006). p21 negatively regulates kinases involved in cell cycle progression by abrogating $G_1/S$ cell cycle transition to provide time for DNA damage repair before cell division. In the presence of irrepairable damage, p53 may induce apoptosis to eliminate damaged cells. In the absence of p53 function, DNA alterations accumulate, leading to initiation or progression of malignancy.

The p53 family includes thus far the founding member, p53, and the more recently recognized closely related members, p63, p73, as well as, numerous isoforms and alternatively spliced versions of each isoform (Murray-Zmijewski et al., 2006). p63 and p73 share many structural and functional features with p53, and activate an overlapping set of genes with p53. p63 is essential in epidermal morphogenesis and limb development, while its relevance in cancer is unclear (Melino et al., 2003). p73 is known to be essential in neuronal development, inflammatory responses and reproductive behaviour (Murray-Zmijewski et al., 2006; Levrero et al., 2000). Both p63 and p73 are capable of activating a cell cycle arrest and apoptotic program akin to that induced by p53.

A prerequisite for p53-mediated transcriptional activation is its ability to specifically bind to a responsive element (RE) within downstream gene promoters that comprises two copies of the palindromic consensus sequence "PuPuPuC(A/T)(T/A)GpyPyPy", separated by 0-13 by (el-Deiry et al., 1992). This same responsive element is also utilized by both p63 and p73 (Murray-Zmijewski et al., 2006; Levrero et al., 2000). After binding to the RE, p53 stimulates the assembly of the transcription preinitiation complex TFIID-TFIIA at the TATA element (Xing et al., 2001). Most of p53 mutations found in human tumors are located in the p53 central domain and affect amino acid residues which contact DNA or are required for the correct folding of p53, thus abolishing the RE binding and transcriptional activation (Cho et al., 1994). p53 has been shown to bind its RE exclusively as a tetramer (Friedman et al., 1993). However, most of the natural p53 REs do not fit completely the consensus sequence (Kim et al., 1997), and other factors, such as p53 modifications, chromatin modifications and folding, and binding of other co-regulatory factors at specific promoter sites, determine the extent of transcriptional response. This also mechanism of action also applies to both p63 and p73 and both are capable of utilizing the RE-element for sequence specific binding, they also regulate a large set of targets specific for each isoform.

Over 50% of human tumors harbor TP53 mutations, which render the p53 protein functionally impaired. This makes TP53 the most commonly mutated gene in human cancers. It is also speculated that the remaining human tumors have dysfunctional p53, through disturbed regulation of the p53 pathway or protein or modifiers of the p53 protein-protein interactions. The essential role of p53 in tumor suppression is evidenced also by TP53 germline mutations, which cause a rare hereditary cancer predisposition, Li-Fraumeni syndrome, and in p53-deficient animal models having severely enhanced tumorigenesis.

Due to its apoptosis inducing properties, p53 is an extremely attractive target for drug development. One particular drug compound, nutlin-3a (Vassilev et al., 2004), is a highly specific activator of p53, and we have established that nutlin-3a is the first and highly effective agent inducing B-cell lymphoma (Kaposi's sarcoma herpes virus-infected pleural effusion lymphoma) cell killing both in vitro and in vivo mouse models (Sarek et al., 2007). Furthermore, activation of the p53 pathway using nutlin-3a does not cause any adverse side-effects in the mouse. Based on these studies it has been concluded that inactivation of the p53 pathway by the KSHV virus lies in the pathogenesis of this incurable malignancy.

Considering that
i) p53 is a highly responsive molecule to cellular stress and DNA damage, implicated in diverse diseases like cancer, ischemia, neuronal disorders, inflammation and also during physiological processes like in normal cellular metabolism, development and aging (Vousden and Lane, 2007),
ii) p53 is a key activator of cell cycle arrest/apoptosis pathways and pathways implicated in the abovementioned processes,
iii) its mutations are uncommon in several common chemotherapy-resistant human cancers (e.g. melanoma, prostate cancer), iv) its activation in conditional mouse models has significant potency in causing tumor regression (Martins et al. 2006, Ventura et al. 2007, Xue et al. 2007), and v) that pilot studies using p53-activating compounds such as nutlin-3a (Vassilev et al. 2004, Sarek et al., 2007) show remarkable in vivo anti-tumor effects without side-effects, further development of small-molecule compounds affecting p53 pathway is highly warranted and has potential for therapeutic exploitation.

SUMMARY OF THE INVENTION

DETAILED DESCRIPTION OF THE INVENTION

Figure 1:
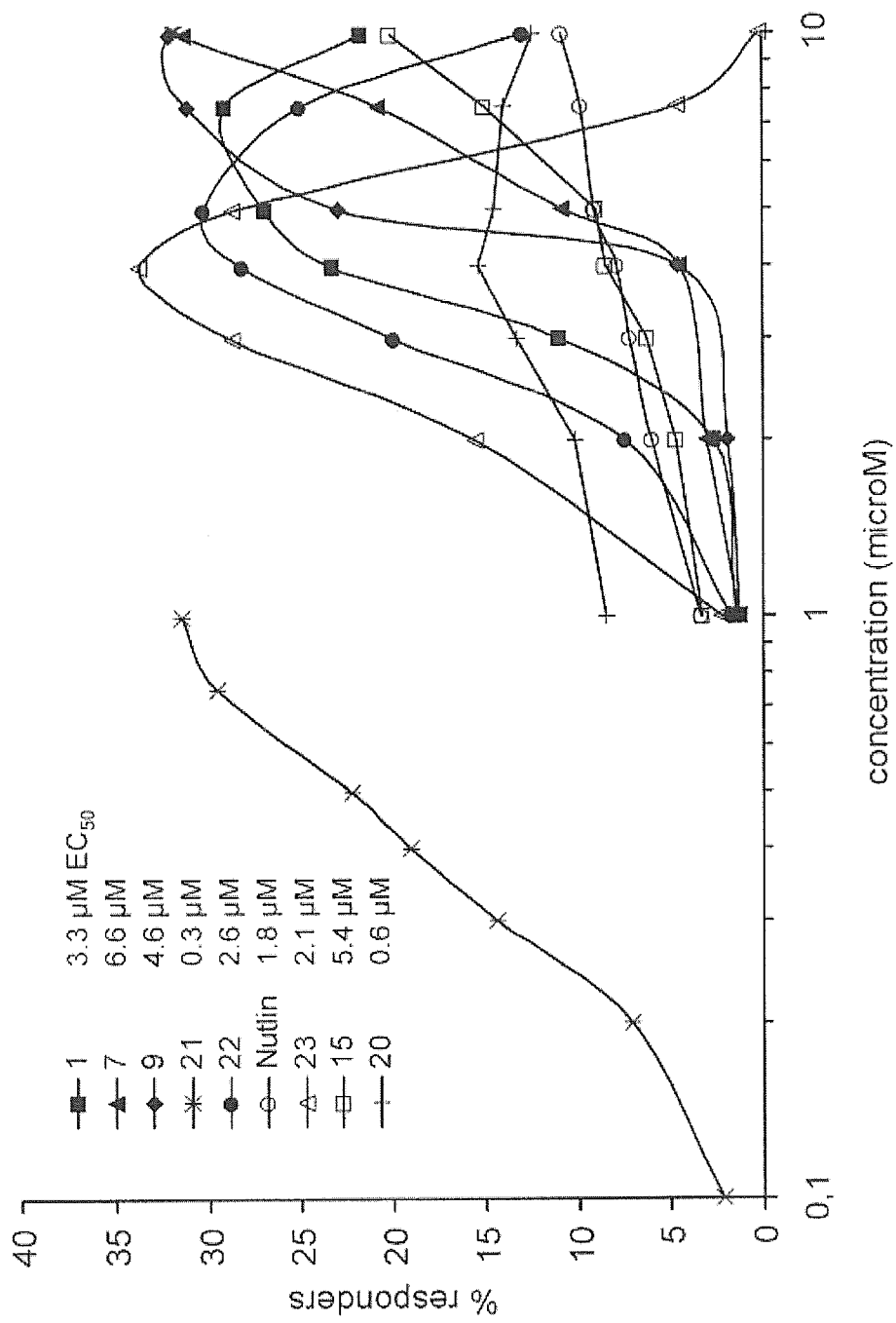
FIG. 1. p53DsRed reporter activation by the compounds. PG3/9 melanoma cells were incubated with the indicated concentrations of compounds 1, 7, 9, 15, 20, 21, 22, 23 and nutlin-3a for 24 hours, followed by the analysis of percentage of cells with activated p53DsRed reporter. The experiment was performed in triplicate and scored using an automated cell-based platform from ≥1700 events per datapoint. SD<10.6.

To achieve the instant invention, key questions about the p53 family members, such as how the proteins are regulated and activated need to be considered. Based on this knowledge, new strategies for therapeutic interventions can be developed. The approach undertaken with the present invention explored ways to activate, or further enhance the activation of pathways affecting wild type p53 (or p63 and p73) in order to launch the downstream transcriptional programs and other ensuing events, including e.g. cell cycle arrest, apoptosis, oxidative and metabolic responses.

A first object of the instant invention was to develop an assay for the high through-put screening of small molecules, which regulate the p53 family pathway. The assay is a cell-based assay the measures for the activation of p53, p63 or p73.

A second object of the invention was to identify small molecular compounds, which activate p53-pathway and sensitise cells by activating the p53 pathway response. To do so, a high-throughput chemical library screen was done with the assay of the invention.

A third of object of the invention is a method of regulating, in particular, activating upstream p53 pathways using the thus identified small molecules.

A fourth object of the invention is a method affecting p53 pathway responses by exposing the cells to the small molecules of the invention. Included is the method directed to induce cell death or arrest of the cells by exposing the cells to the small molecule. Of particular interest with the present invention is a method of controlling cells with the small molecules identified.

A fifth object of the invention is a method of treating diseases or conditions that are responsive to the activation of p53 pathway by administering to a human or non-human patient in need thereof an effective amount of the small molecule of the invention. Of particular interest is a method of treating cancer, and noting the wide-spectrum of p53 activities in other physiological and disease states, such as ischemic states, neuronal disorders, inflammation, cellular metabolism, development and aging, also of those which require controlled activation of the p53 pathway.

Tied to the fifth object of the invention, a further object of the invention is a pharmaceutical composition, which contains the small molecules along with a phaimaceutically acceptable carrier thereof.

The small molecule compounds listed in Table 1, below are of particular interest for use in the methods of regulating p53 pathway and methods of treatment of the invention.

| Compound ID | Structure | Name (IUPAC) | Formula |
|---|---|---|---|
| 1 | 5-methoxy-1-methyl-1H-pyrazolo[4,3-b]quinolin-9-amine | 5-methoxy-1-methylH-pyrazolo[4,3-b]quinolin-9-amine | C12H12N4O |
| 7 | 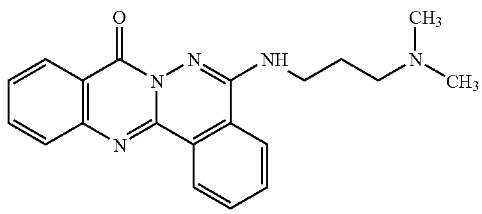 [SMILES: CN(C)CCCNc1nn2c(=O)c3ccccc3nc2c2ccccc12] | | C20H21N5O |
| 9 | 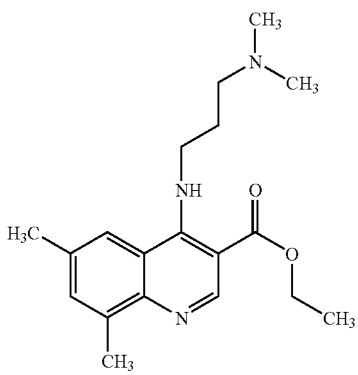 [SMILES: CCOC(=O)c1cnc2c(C)cc(C)cc2c1NCCCN(C)C] | ethyl 4-(3-dimethylaminopropylamino)-6,8-dimethyl-quinoline-3-carboxylate | C19H27N3O2 |
| 15 | 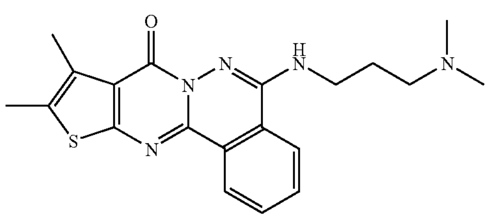 | | C20H23N5OS |
| 20 | 5-(4-ethoxyphenyl)-7-(3,4,5-trimethoxyphenyl)-4,7-dihydro-[1,2,4]triazolo[1,5-α]pyrimidine | 5-(4-ethoxyphenyl)-7-(3,4,5-trimethoxyphenyl)-4,7-dihydro-[1,2,4]triazolo[1,5-α]pyrimidine | |

-continued

| Compound ID | Structure | Name (IUPAC) | Formula |
|---|---|---|---|
| 21 | 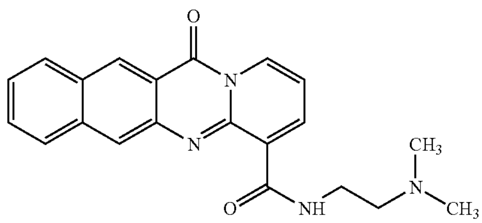 [SMILES: CN(C)CCNC(=O)c1cccn2c(=O)c3cc4ccccc4cc3nc12] | | C21H20N4O2 |
| 22 | 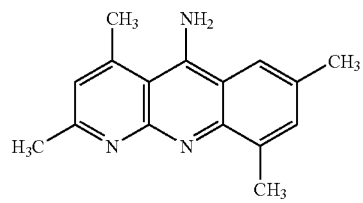 | 2,4,7,9-tetramethylbenzo[b]-1,8-naphthyridin-5-amine | C16H17N3 |
| 23 | 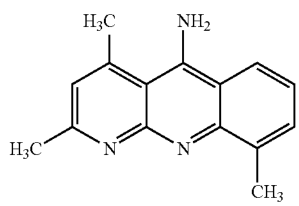 | 2,4,9-trimethylbenzo[b]-1,8-naphthyridin-5-amine | C15H15N3 |

In addition to the specific listed compounds above, also included in the invention are near homologues and positional isomers of the compounds that have equal or more potent therapeutic applicability. Near homologues are compounds that differ, for example, by the replacement of a chemical moiety on the compound with a successive chemical moiety, for example, the replacement a methyl group with an ethyl group or visa versa. Also included in the invention are pharmaceutically acceptable salts, esters and prodrugs of the compounds.

The amount of the small molecule of the invention used for therapeutic applications varies with standard considerations, such as the nature of the condition being treated, and the age and the condition of the patient, and is ultimately determined by the attendant physician. In general, however, doses employed for adult human treatment typically are in the range of about 0.001 mg/kg to about 200 mg/kg per day, with a preferred dose being about 1 µg/kg to about 100 µg/kg per day. The desired dose can be conveniently administered in a single dose, or as multiple doses administered at appropriate intervals, for example as two, three, four or more subdoses per day. Formulations of the present invention can be administered in a standard manner, such as orally, parenterally, sublingually, transdermally, rectally, transmucosally, topically, via inhalation, or via buccal administration.

For example, the pharmaceutical compositions of the present invention can be formulated for parenteral administration by injection or continuous infusion. Formulations for injection can be in the form of suspensions, solutions, or emulsions in oily or aqueous vehicles, and can contain formulation agents, such as suspending, stabilizing, and/or dispersing agents. Alternatively, the active ingredient can be in powder form for reconstitution with a suitable vehicle (e.g., sterile, pyrogen-free water) before use.

The pharmaceutical composition of the invention can also be in the form of tablets or lozenges formulated in conventional manner and techniques. For example, tablets and capsules for oral administration can contain conventional excipients such as binding agents (for example, syrup, accacia, gelatin, sorbitol, tragacanth, mucilage of starch or polyvinylpyrrolidone), fillers (for example, lactose, sugar, microcrystalline cellulose, maize-starch, calcium phosphate, or sorbitol), lubricants (for example, magnesium stearate, stearic acid, talc, polyethylene glycol, or silica), disintegrants (for example, potato starch or sodium starch glycollate), or wetting agents (for example, sodium lauryl sulfate). Similarly, the small molecules of the present invention can be incorporated into liquid preparations such as aqueous or oily suspensions, solutions, emulsions, syrups, or elixirs, using conventional techniques and carriers. Such liquid preparations can contain conventional additives, like suspending agents, such as sorbitol syrup, methyl cellulose, glucose/sugar syrup, gelatin, hydroxyethylcellulose, carboxymethyl cellulose, aluminum stearate gel, and hydrogenated edible fats; emulsifying agents, such as lecithin, sorbitan monooleate, or acacia; nonaqueous vehicles (which can include edible oils), such as almond oil, fractionated coconut oil, oily esters, propylene glycol, and ethyl alcohol; and preservatives, such as methyl or propyl p-hydroxybenzoate and sorbic acid.

The present pharmaceutical compositions may also be in the form of suppositories with conventional suppository bases, such as cocoa butter or other glycerides or in a form to be administered through inhalation, typically in the form of a solution, suspension, or emulsion that can be administered as a dry powder or in the form of an aerosol using a conventional propellant. Typical transdermal formulations comprise conventional aqueous or nonaqueous vehicles, and are in the form of creams, ointments, lotions, pastes, medicated plasters, patches, or membranes.

The pharmaceutical compositions of the invention may contain one or more than one of the small molecules of the invention. In addition, the pharmaceutical compositions may contain additional active agents, which are active in treating the target disease. For example, additional cancer therapeutic agents or agents active for treating side effects associated with the drug therapy may be included in the pharmaceutical composition or may be administered simultaneously, but in a separate preparation, or sequentially to the pharmaceutical composition containing the small molecules of the invention.

Experimental Embodiments of the Invention

In Vitro p53 Activity Assay

The ability of the compounds to activate p53 was analyzed using a cell-based assay. To establish the assay, a stable cell transfectant expressing a p53-responsive reporter was generated. A375 melanoma cell line (ATCC CRL-1619) was transfected with a vector containing the p53 consensus element 13× repeat (13XRE) (Kern et al., 1991) cloned to a DsRed Express reporter vector (Clontech) to yield the vector "PG13DsRed", hereafter termed as "p53DsRed". Stable cells clones were selected in the presence of G418 (Calbiochem), and G418 resistant clones were analysed for p53DsRed reporter activation by UVC and gamma radiation ($^{137}$Cs source) as well as using a small-molecule compound inhibiting p53-Mdm2 interaction, nutlin-3a (Alexis) (Vassilev et al., 2004). The cell clone PG3/9 was used in the screen.

The assay was carried out in a 96-well format and all plate handlings were done using liquid handling robots (Thermo CRS, Thermo Electron Corporation; Biomek FX, Beckman Coulter and Hamilton STAR, Hamilton Microlab). Cells were plated at 10,000 cells/100 µL/well onto 96-well ViewPlates (Packard) and incubated overnight at +37° C. and 5% $CO_2$. Small molecule compound chemical libraries were purchased and diluted to dimethylsulfoxide (DMSO) at 10 mM concentration. The compounds were pin-transferred to plain media at approximately 3 µM concentration either as single (one compound/one well) or pools of compounds (two compounds/one well). The growth media was removed and replaced with media with the test compounds followed by incubation of the cells for 24 h at +37° C. and 5% $CO_2$. Mock treatment (DMSO alone) and positive controls (3 µM nutlin-3a) were included in each 96-well plate. Following the incubation, the cells were washed with phosphate buffered saline and fixed with paraformaldehyde (PFA, 4%, 25 min, RT) and cell nuclei were stained with Hoechst 33342 (Molecular Probes, 4 µg/mL, 2 min, RT).

The fluorescence signals of Hoechst 33342 and DsRed reporter expression in the fixed cells were analyzed using ArrayScan 4.5 high-content screening platform (Cellomics) including an inverted microscope (Zeiss 200M) with 10× objective (Zeiss), Omega XF93 filter (Omega), ORCA-AG CCD camera (Hamamatsu). The algorithm used for image acquisition and analysis was Target Activation Bioapplication (Cellomics), which was set to analyse the total number of cells and the percentage of p53 reporter positive cells termed as "responders". For each well, four images on both fluorescence channels were acquired corresponding to approximately 1700 cells in mock-treated wells. The mean number of responders was calculated for each well, and compounds causing reporter activation for more than two times the mean number of responders in the mock treated cells in each plate were regarded as hits.

In the secondary screen the hits were collected and tested over 100 nM to 10 µM concentration range. The compound treatment time, cell fixations and stainings as well as fluorescence signal detection was as described above. Compounds providing consistent p53DsRed reporter activation at low µM concentration range were selected for further testing. The effective concentration 50 (EC50) was calculated using the following formula:

$$EC50 = \frac{(50\% \text{ max. induction} - \text{high }\% \text{ ind.})}{(\text{low }\% \text{ ind.} - \text{high }\% \text{ inc.})} \times (\text{low } conc. - \text{high } conc.) + \text{high } conc.$$

Viability Assays

The effect of the compounds selected using the screening assay on the viability of several tumor cell lines as well as diploid cell lines and cell strains was studied. Cells were plated in 96-well plates at a density of 10,000 cells/100 µL/well and were incubated overnight. The following day compound dilutions ranging from 0 to 40 µM were applied to the cells in triplicate and the cells were incubated with the compounds for three days. Cell viability was assayed using the WST-1 cell proliferation reagent (Roche Diagnostics, Germany). The WST-1 reagent was diluted 1:10 in cell culture media and 100 µL of the reagent dilution was applied onto cells followed by 1 hour incubation at +37° C. The specific absorbance was measured at 450 nm and a reference absorbance was measured at 690 nm. The experiment was repeated two to three times and results are presented as % viability compared to the control. IC50 values representing 50% inhibitory concentration were calculated using the formula:

$$IC50 = \frac{(50 - \text{low }\% \text{ inhibition})}{(\text{high }\% \text{ inh.} - \text{low }\% \text{ inh.})} \times (\text{high } conc. - \text{low } conc.) + \text{low } conc.$$

Analysis for Protein Levels

To study the effect of compounds on endogenous protein levels, A375 melanoma cells were treated with the compounds for 24 hours. Cellular lysates were prepared in lysis buffer containing 0.5% NP-40 with proteinase inhibitors. Protein (20-30 µg) was separated by sodium dodecyl sulphate-polyacrylamide gel electrophoresis (SDS-PAGE) followed by transfer to PVDF membrane (Immobilon™-P, Millipore, Bedford, Mass., USA). Immunoblotting was carried out using DO-1 antibody for p53, 2A10 for Mdm2 and anti-p21 (Becton Dickinson) to detect p21, followed by secondary antibodies conjugated with horseradish peroxidase (p53) or biotin followed by streptavidin-horseradish peroxidase (Mdm2 and p21) after which proteins were detected with enhanced chemiluminescence (ECL, Amersham Life Sciences). Equal protein loading was verified using GAPDH (p9.B.88, Europa Bioproducts Ltd, UK) as a protein loading control.

Flow Cytometry and Immunofluorescence

Cell cycle analysis and cellular apoptosis was assayed with flow cytometry (LSR, Beckton Dickinson). Cells were treated with the compounds and both floating and adherent cells were harvested and fixed in 70% ethanol at −20° C. followed by staining of DNA with propidium iodide. A total of 10,000 counts were collected and data was analysed using ModFit LT 3.1 software. Cells present in sub-$G_1$ population were regarded as apoptotic.

Immunofluorescence staining was carried out to determine the correct localisation of p53 and to detect H2AX phosphorylation indicative of genotoxic stress. Cells were treated with the compounds and fixed in paraformaldehyde (3.5 PFA, 25 min RT). The coverslips were permeabilised in 0.5% NP-40 and blocked in 3% bovine serum albumin (BSA). p53 was detected by staining with FL-393 antibody (Santa Cruz, 1:50, 1 h at +37° C.) followed by Alexa-594 conjugated secondary antibody (Molecular Probes, 1:200, 1 h at +37° C.), phospho-H2AX was detected by staining with anti-H2AX (P-Ser-139) antibody (Upstate, 1:200 1 h at +37° C.) followed by Alexa-488 conjugated secondary antibody (Molecular Probes, 1:200, 1 h at +37° C.). Nuclei were stained with Hoechst 33342. Images were captured using the Zeiss Axioplan fluorescence microscope equipped with Zeiss AxioCam HRc CCD-camera and AxioVision 4.5 software using 40×, NA=0, 75 objective, Chroma 31000, Chroma41001 and 41004 filters for Hoechst, Alexa488 and Alexa594, respectively.

In Vivo Toxicity Tests

Acute and chronic toxicity of the compounds was tested on FVB/N mice. Female mice of 4-6 weeks old were purchased from Harlan and 2 animals were used per compound dose. The mice were injected intraperitoneally with the compounds three times a week for three weeks in 30 microL DMSO. Two animals received vehicle only (=30 µL, DMSO). The animals were weighed prior to injections and were monitored for any signs of toxicity, distress or unusual behaviour. The animals were sacrificed three days after receiving the final injection. The liver, kidney, spleen, small intestine and thymus were excised and fixed in 4% paraformaldehyde overnight, and processed into paraffin-blocks. Haematoxylin-eosin staining (HE staining) of the tissues was performed using standard immunohistological techniques.

In Vivo Tumor Model

An orthotopic xenograft model of pleural effusion lymphoma was used to assess the anti-tumor activities of compounds 15, 21 and 22. Female NOD-SCID mice (Charles River, France) were injected intraperitoneally with pleural effusion lymphoma cells carrying a stable NF-kappaB regulated luciferase reporter (BC3-luc cells) (Keller et al., 2006). The tumors were allowed to establish for three days after which the mice were imaged and divided into treatment (groups 4-5 mice per group). The compound treatments were initiated on day four, The mice received 2 mg/kg (cmp 21) or 20 mg/kg (cmp15 and 22) every other/third day for seven times via i.p. injections, control mice received DMSO only. The mice were imaged prior to each compound injection. Imaging was carried out with Xenogen In Vivo Imaging System (IVIS), D-luciferin (Synchem OHG, Germany) was injected intraperitoneally (100 mg/kg) 10-15 min prior to each imaging. Quantitation was done using Igor Pro Carbon analysis software, bioluminescence was quantitated and plotted as total flux within a given ROI.

Results

Following an initial high-throughput screen of 40,000 compounds and analysis of reporter activation in a cell-based assay by high-content image analysis, several compounds of interested were identified and designated as compounds 1, 7, 9, 15, 20, 21, 22, 23. The structures of compounds 1, 7, 9, 15, 20, 21, 22, 23 are shown in Table 1.

These compounds have been validated as potent (i.e. low µM-nM range) activators of p53-reporter activity. As shown in FIG. 1, each compound (cmp) induces p53-reporter in melanoma cells with a capacity that equals or exceeds that of a positive control compound, nutlin-3a. The respective effective concentrations (EC50) for each compound are as follows; cmp 1, 3.3 µM; cmp 7, 6.6 µM; cmp 9, 4.6 µM; cmp 15, 5.4 µM; cmp 20, 0.6 µM cmp 21, 0.3 µM; cmp 22, 2.6 µM; cmp 23, 2.1 µM. With high concentrations of compounds 1, 22, and 23 a decrease in the fraction of p53-reporter activated cells was detected, apparently due to excessive cell death (not shown).

Figure 2:
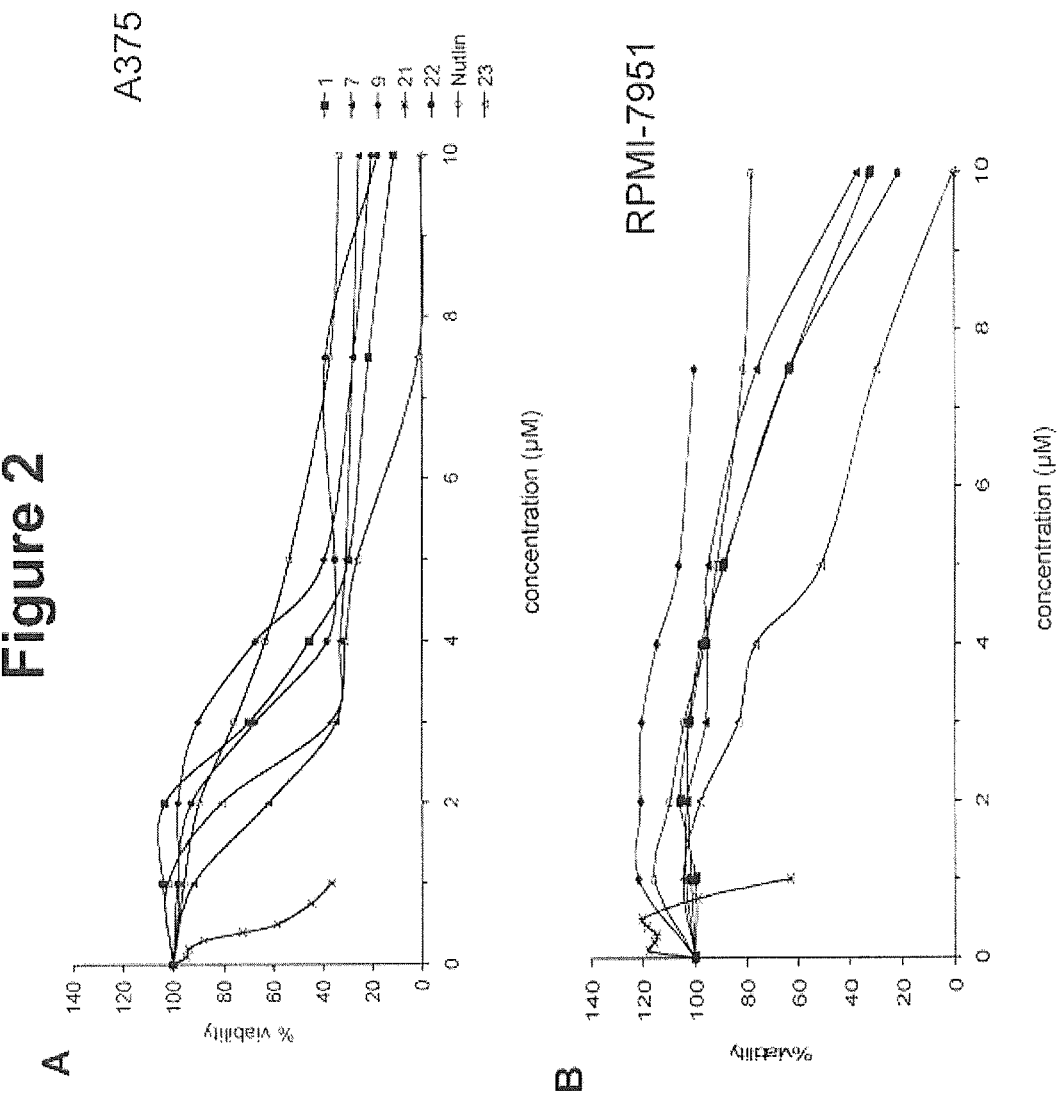
FIG. 2. The small molecule compounds decrease melanoma cell viability in a p53-dependent manner. A375 (A) and RPMI-7951 (B) cells were incubated with the indicated concentrations of compounds 1, 7, 9, 21, 22, 23 and nutlin-3a in triplicate for three days, followed by cell viability assay using WST-1 cell proliferation reagent.

The effects of the compounds using cell viability tests on two melanoma cell lines, one which expresses wild-type p53 (A375) and one which has a p53 truncation mutation and does not produce a functional p53 (RPMI-7951) were compared. All tested compounds were able to decrease cell viability of the wt p53 melanoma cell line, and were more or equally potent as nutlin-3a (FIG. 2A). However, the compounds were clearly much less efficient in decreasing cell viability of the melanoma cell line with mutant p53 (FIG. 2B).

Figure 3:
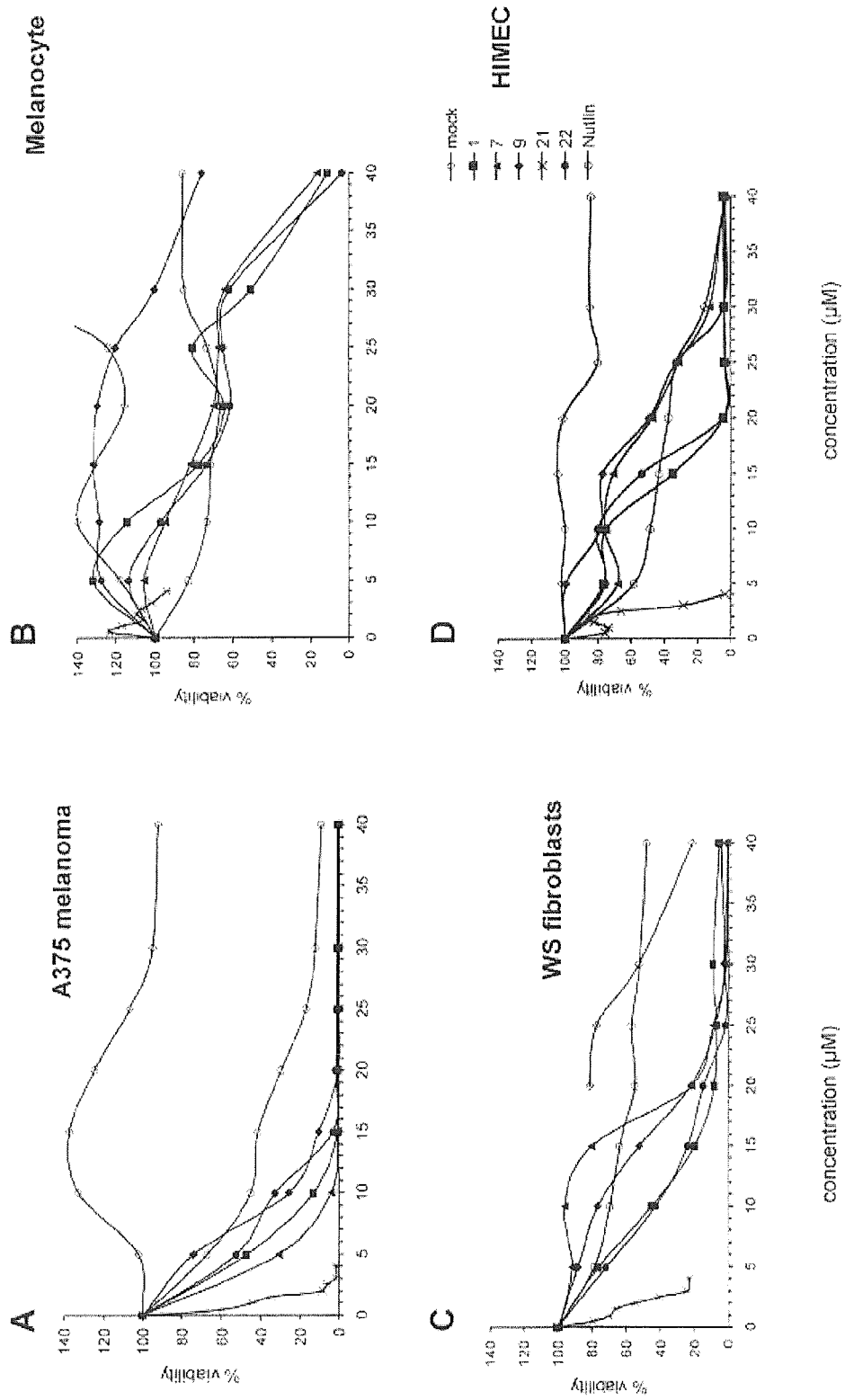
FIG. 3. Cell viability tests of the small molecule compounds in normal human cells. Cells were incubated with the indicated concentrations of compounds 1, 7, 9, 21, 22 and nutlin-3a in triplicate for three days, followed by cell viability assay using WST-1 cell proliferation reagent. (A) A375 melanoma cells, (B) normal human primary melanocytes, (C) WS-1 normal diploid fibroblasts, (D) human primary intestinal endothelial cells.

Potential toxicities of the compounds in several non-transformed human cell lines that express wild type p53 were also tested. These included melanocytes, fibroblasts and human intestinal endothelial cells. The cells were incubated with the indicated concentrations of the compounds for three days, followed by cell viability measurements. For each compound, the 1050 was lower for the A375 melanoma cells than for the normal human cell lines (FIG. 3, Table 2). Furthermore, each compound was ≥2.4 fold more potent in decreasing melanoma cell viability as compared to the most sensitive normal cell line (WS-1 cells) (Table 2).

TABLE 2

Figure 4:
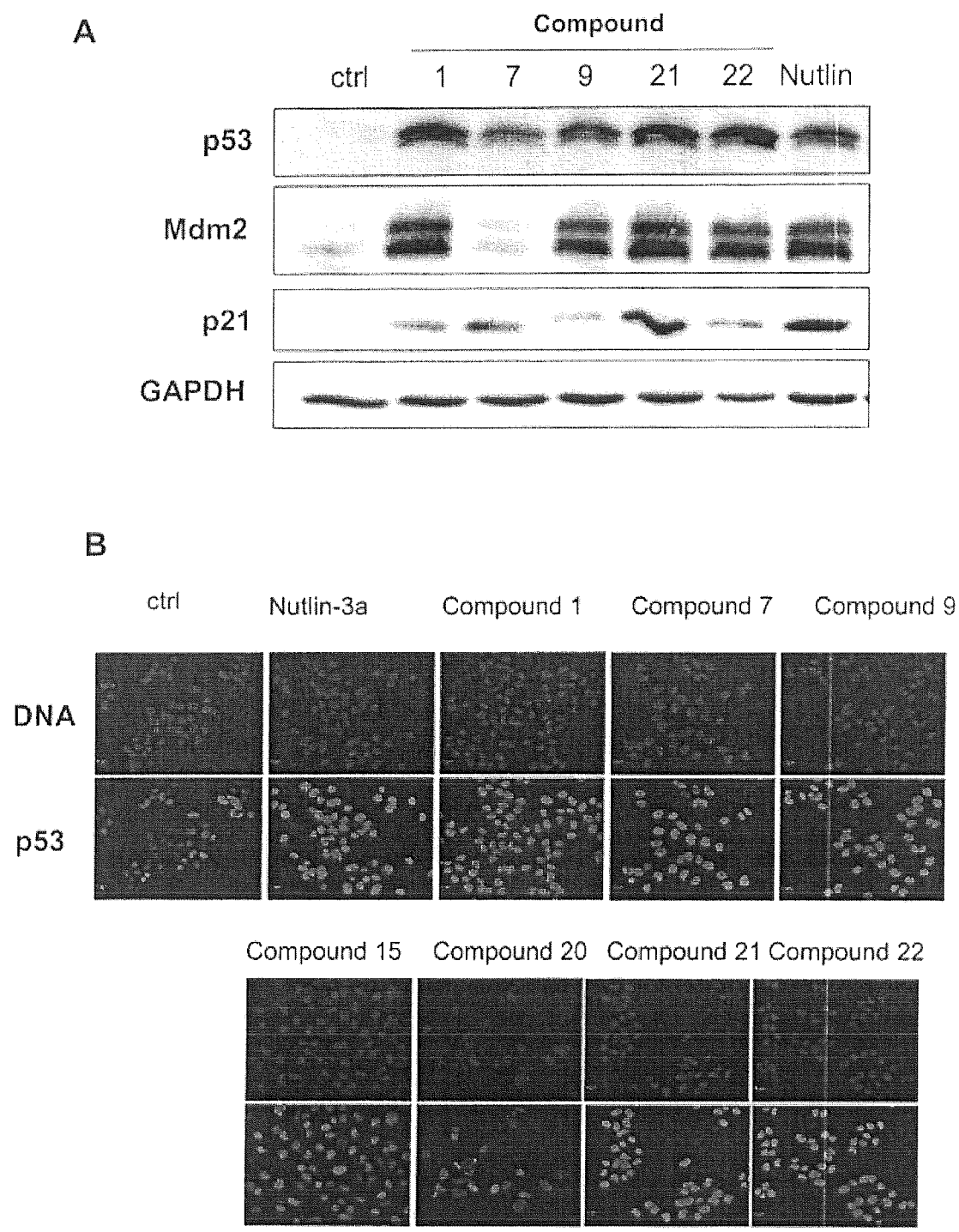
FIG. 4. Small molecule compounds activate the p53-pathway. A375 melanoma cells were treated with compounds 1, 7, 9, 15, 20, 22 (5 µM) and with compound 21 (0.5 µM) for 24 hours followed by immunoblotting analyses for p53, Mdm2 and p21 levels (A) or immunofluorescence staining for p53 (B). GAPDH was used as a protein loading control (A). Nuclei were stained with Hoechst 33342 (B).

| Cell line | | Compound | | | | | |
|---|---|---|---|---|---|---|---|
| | | 1 | 7 | 9 | 21 | 22 | Nutlin |
| A375 melanoma (WTp53) | IC50 | 4.3 | 3.0 | 6.1 | 0.7 | 4.6 | 7.2 |
| | SD | 0.6 | 0.8 | 2.0 | 1.1 | 1.4 | 2.4 |
| RPMI7951 (MUTp53) | IC50 | 14.7 | 16.8 | 17.8 | 3.0 | 13.3 | >40 |
| | SD | 4.1 | 4.0 | 1.5 | 2.1 | 1.3 | |
| WS-1 diploid fibroblast | IC50 | 10.4 | 18.1 | 15.7 | 1.9 | 11.5 | 20.6 |
| | SD | 4.8 | 2.6 | 5.0 | 3.6 | 5.7 | 6.9 |
| Melanocyte | IC50 | 30.4 | 32.4 | >40 | >40 | 32.2 | >40 |
| | SD | 1.8 | 1.1 | | | 0.7 | |
| Human intestinal endothelial cells | IC50 | 13.1 | 19.6 | 19.6 | 2.7 | 14.5 | 10.7 |
| | SD | 0.8 | 2.8 | 1.6 | 5.1 | 2.0 | 10.7 |
| | fold difference IC50 (A375)/ IC50 (WS-1) | 2.4 | 6.0 | 2.6 | 2.6 | 2.5 | 2.9 | p53 activation is frequently observed in conjunction with a significant increase in its protein levels. We therefore assessed for the levels of p53 and for possible induction of its target genes, Mdm2 and p21. A375 melanoma cells were incubated for 24 hours with the indicated compounds, cell lysates were prepared and analysed by immunoblotting with p53, Mdm2 and p21 antibodies. All tested compounds significantly increased the level and nuclear accumulation of p53 (FIGS. 4A and B). Furthermore, all compounds induced p53 target gene expression but to a different extent. Induction of p21 cyclin kinase inhibitor was most prominent with compound 21, and Mdm2 induction was most prominent with compounds 1, 9, 21 and 22 (FIG. 4A). Differences in the capacity of the compounds to induce Mdm2 and p21 are indicative that the compounds may utilize mechanistically different pathways for the induction of p53.

Figure 5:
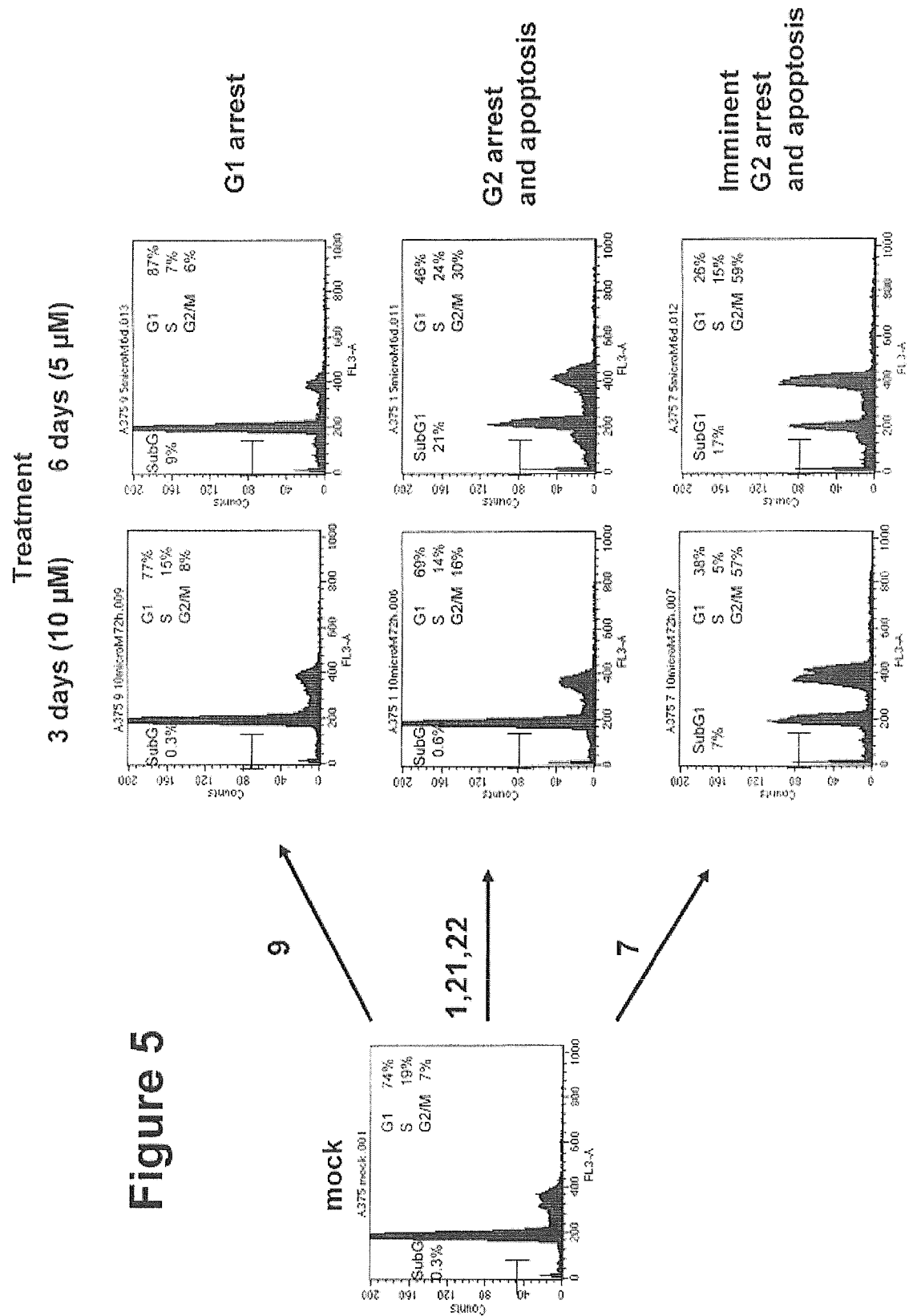
FIG. 5. Small molecule compounds cause cell cycle arrest and apoptosis. A375 melanoma cells were treated with compounds 1, 7, 9, and 22 for three days (at 10 µM concentration) or for six days (at 5 µM concentration) followed by flow cytometry analyses. Treatment doses for compound 21 were 0.1 µM (three days) and 0.5 µM (six days).

The effect of the compounds on the melanoma cells was assessed using flow cytometry. A375 melanoma cells were treated with the compounds for either 3 or 6 days, followed by propidium iodide staining and flow cytometry analysis. Three different phenotypic responses were detected. Cpm 9 caused a G1-phase arrest of the cells, whereas compounds 1, 21 and 22 caused G2-phase arrest and apoptosis. On the other hand, crop 7 caused an imminent G2-phase arrest and increased the apoptotic fraction of the cells (FIG. 5).

Figure 6:
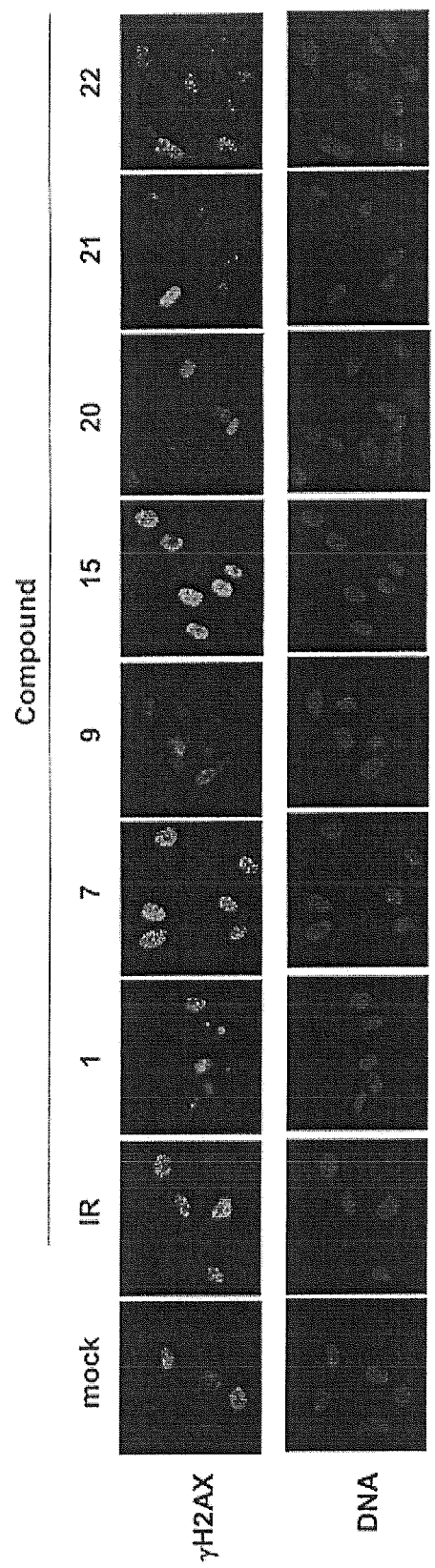
FIG. 6. Compounds 7 and 15 induces genotoxic stress. A375 melanoma cells were treated with compounds 1, 7, 9, 15, 20, 22 (5 µM) and with compound 21 (0.5 µM) for 24 hours. The cells were fixed and stained with an antibody against phospho-H2AX. Nuclei were stained with Hoechst 33342.

Induction of G2-checkpoint is often observed in response to genotoxic stress, like ionizing radiation. As such, whether the compounds induce phosphorylation of histone H2AX on serine-139 (γH2AX), which is a rapid and specific marker for the presence of DNA strand lesions, was tested. Cmps 7 and 15 induced a cellular γH2AX response concordant with the induction of G2-phase arrest (FIG. 6). Together, the results are indicative that cmps 7 and 15 induce p53-pathway through a genotoxic stress response. It is possible that the other compounds activate p53 pathway through other cellular stress activating pathways by other means than causing DNA double strand breaks.

Figure 7:
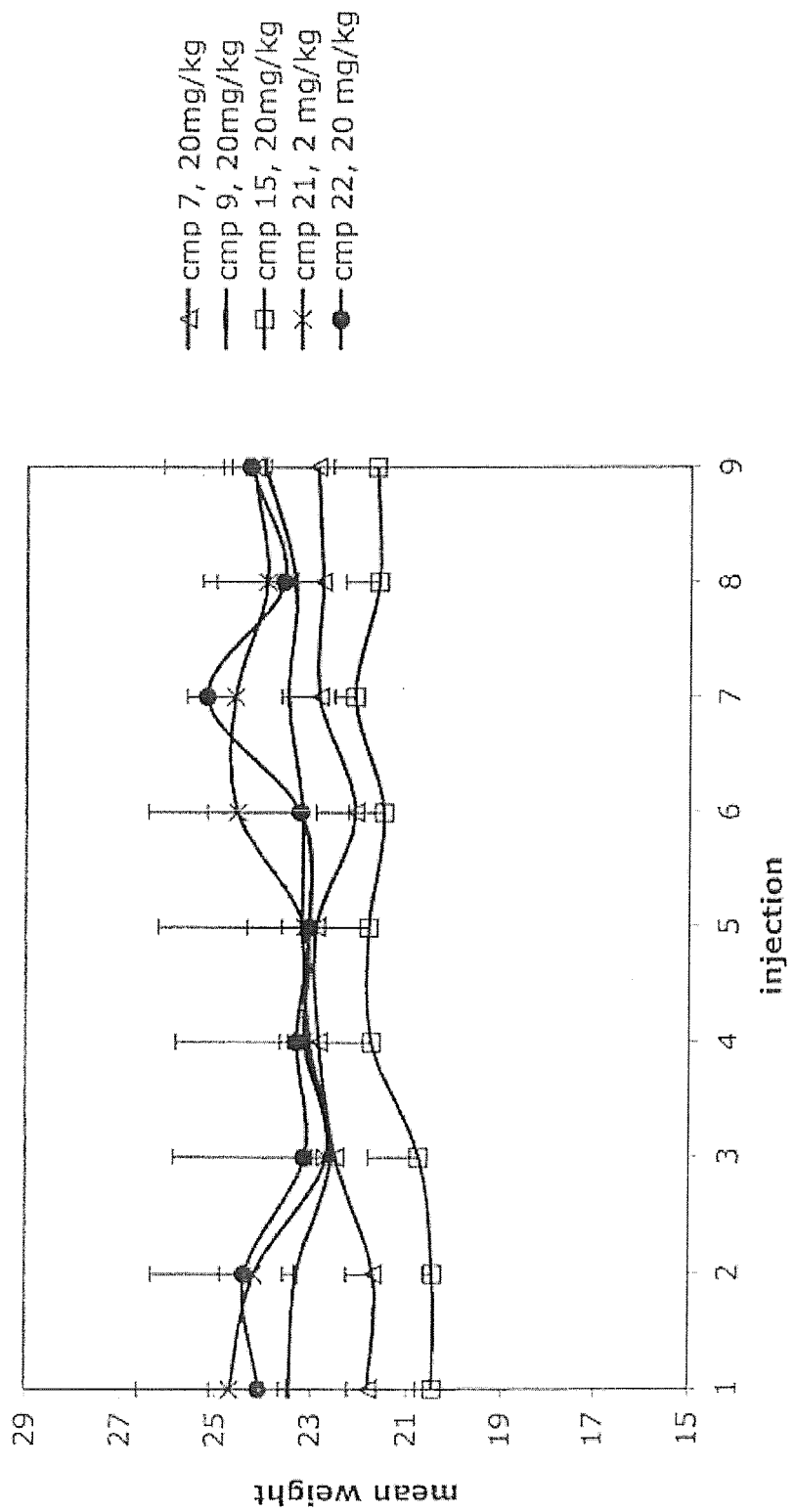
FIG. 7. In vivo toxicity tests. Mice were injected intraperitoneally with compounds 7, 9, 15 and 22 (5, 10 and 20 mg/kg) and compound 21 (0.5, 1, 2 mg/kg) three times a week for three weeks in 30 microL DMSO, control mice received DMSO vehicle. The mice were sacrificed and radiosensitive organs (thymus, spleen, intestine) and liver and kidney were collected for further histological examination. No acute or chronic toxicities were observed in the mice based on the histological HE-stainings (data not shown). Weight curves of the animals are plotted.
Figure 8:
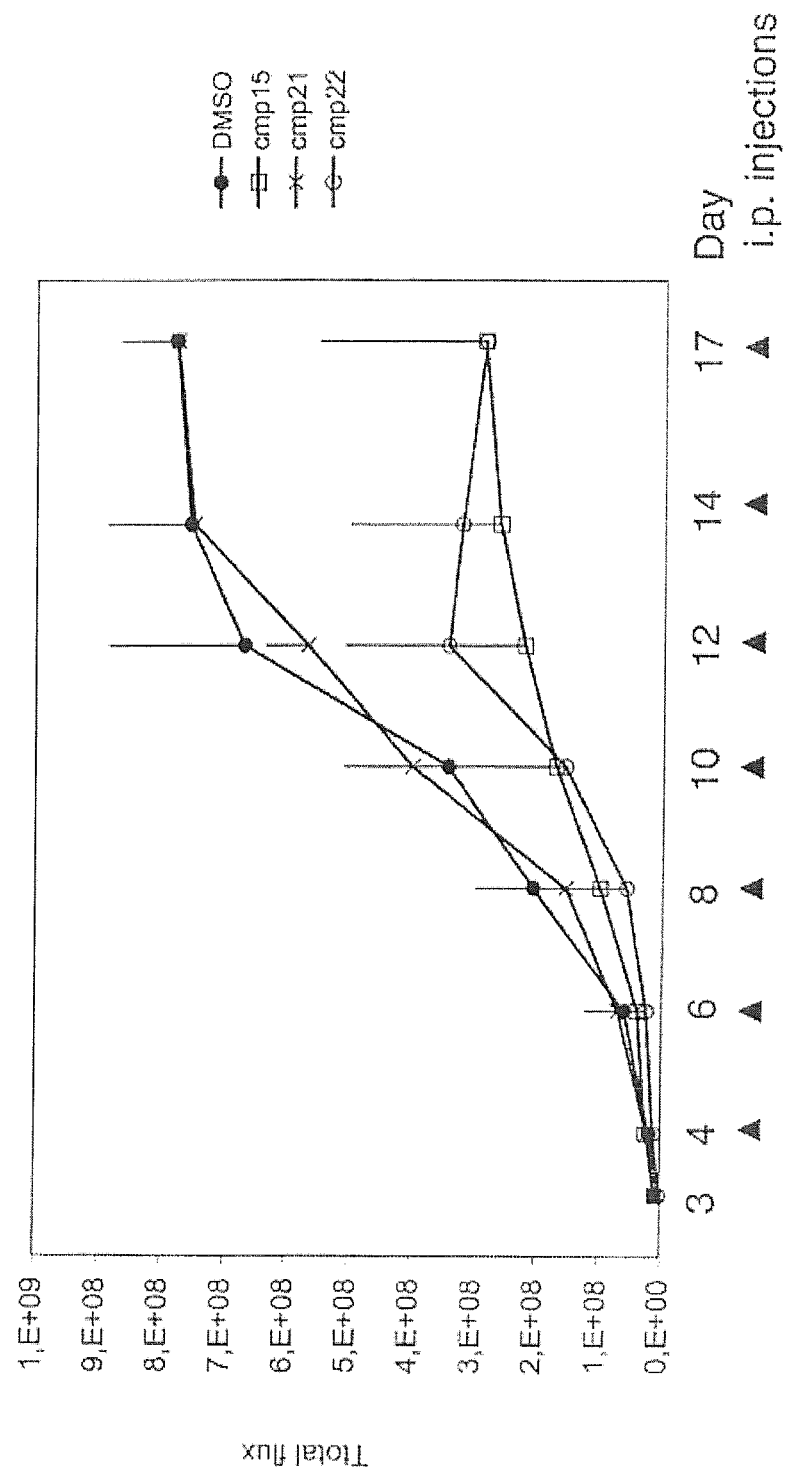
FIG. 8. In vivo anti-tumor activity of the compounds. An orthotopic xenograft model of pleural effusion lymphoma combined with whole animal imaging was used to assess the anti-tumor activities of compounds 15, 21 and 22. Female NOD-SCID mice were injected intraperitoneally with BC3-luc cells and tumors were allowed to establish. As compound treatments the mice received 2 mg/kg (cmp21) or 20 mg/kg (cmp 15 and 22) for seven times via i.p. injections. The mice were imaged prior to each compound injection and bioluminescence was quantitated and plotted as total flux within a given ROI.

With the assay of the invention, potent p53-pathway activating small-molecule compounds were identified. The compounds induce p53 stabilization, sequence-specific binding, reporter activation, and have the capacity to induce p53 target genes. All compounds decrease selectively the viability of tumor cells at low microM concentrations. Together the results confirm that the indicated compounds activate p53 pathway and cause cell cycle arrest and cell death, features of which are beneficial in attempts to restrict tumor cell growth in vitro and in vivo. These effects may be coupled with activation of the cellular DNA damage response. Toxicity tests in mouse using intraperitoneal injections of compounds 7, 9, 15, 21, 22 (9 doses/3 weeks) did not show any apparent toxicity on the animals as indicated by weight curves (FIG. 7), macroscopical pathologies, or hematoxylin-eosin staining of tissues such as thymus, spleen, gut, liver or kidney (not shown). Support for their potential utility as anti-tumor agents is indicated by a orthotopic B cell lymphoma model. The mice were injected with BC-3 pleural effusion lymphoma cells stably integrated with a luciferase reporter gene (Keller et al., 2006). Once the tumors were established, as measured by in vivo bioluminescence monitor, the mice were treated by intraperitoneal injections of the compounds three times a week. Treatment of the animals with compounds 15 and 22 led to noticeable inhibition of the tumor cell growth whereas compound 21 did not have any effect (FIG. 8). The results indicate potential anti-tumorigenic effects by the compounds.

References

Cho Y, Gorina S, Jeffrey P D, Pavletich N P. Crystal structure of a p53 tumor suppressor-DNA complex: understanding tumorigenic mutations. Science. 1994 265:346-55.

el-Deiry W S, Kern S E, Pietenpol J A, Kinzler K W, Vogelstein B. Definition of a consensus binding site for p53. Nat. Genet. 1992 1:45-9.

Friedman P N, Chen X, Bargonetti J, Prives C. The p53 protein is an unusually shaped tetramer that binds directly to DNA. Proc Natl Acad Sci USA. 1993 90:3319-23.

Haapajarvi T, Pitkanen K, Laiho M. Human melanoma cell line UV responses show independency of p53 function. Cell Growth Differ 1999 10:163-71.

Keller S A, Hernandez-Hopkins D, Vider J, Ponomarev V, Hyjek E, Schattner E J, Cesarman E. NF-kappaB is essential for the progression of KSHV- and EBV-infected lymphomas in vivo. Blood. 2006 107:3295-302.

Kern S E, Kinzler K W, Bruskin A, Jarosz D, Friedman P, Prives C, Vogelstein B. Identification of p53 as a sequence-specific DNA-binding protein. Science. 1991 252:1708-11.

Kim E, Albrechtsen N, Deppert W. DNA-conformation is an important determinant of sequence-specific DNA binding by tumor suppressor p53. Oncogene. 1997 15:857-69.

Levrero M, De Laurenzi V, Costanzo A, Gong J, Wang J Y, Melino G. The p53/p63/p73 family of transcription factors: overlapping and distinct functions. J Cell Sci. 2000 113:1661-70.

Martins C P, Brown-Swigart L, Evan G I. Modeling the therapeutic efficacy of p53 restoration in tumors. Cell 2006 127:1323-34.

Melino G, Lu X, Gasco M, Crook T, Knight R A. Functional regulation of p73 and p63: development and cancer. Trends Biochem Sci. 2003 28:663-70.

Murray-Zmijewski F, Lane D P, Bourdon J C. p53/p63/p73 isoforms: an orchestra of isoforms to harmonise cell differentiation and response to stress. Cell Death Differ. 2006 13:962-72.

Sarek G, Kurki S, Enback J, Iotzova G, Haas J, Laakkonen P, Laiho M, Ojala P M. Reactivation of the p53 pathway as a treatment modality for KSHV-induced lymphomas. J Clin Invest. 2007 117:1019-28.

Vassilev L T, Vu B T, Graves B, Carvajal D, Podlaski F, Filipovic Z, Kong N, Kammlott U, Lukacs C, Klein C, Fotouhi N, Liu E A. In vivo activation of the p53 pathway by small-molecule antagonists of MDM2. Science. 2004 303:844-8.

Ventura A, Kirsch D G, McLaughlin M E, Tuveson D A, Grimm J, Lintault L, Newman J, Reczek E E, Weissleder R, Jacks T. Restoration of p53 function leads to tumour regression in vivo. Nature 2007 445:661-5.

Vousden K H, Lane D P. p53 in health and disease. Nat Rev Mol Cell Biol. 2007 8:275-83.

Wang L, Wu Q, Qiu P, Mirza A, McGuirk M, Kirschmeier P, Greene J R, Wang Y, Pickett C B, Liu S. Analyses of p53 target genes in the human genome by bioinformatic and microarray approaches. J Biol. Chem. 2001 276:43604-10.

Wei C L, Wu Q, Vega V B, Chiu K P, Ng P, Zhang T, Shahab A, Yong H C, Fu Y, Weng Z, Liu J, Zhao X D, Chew J L, Lee Y L, Kuznetsov V A, Sung W K, Miller L D, Lim B, Liu E T, Yu Q, Ng H H, Ruan Y. A global map of p53 transcription-factor binding sites in the human genome. Cell. 2006 124:207-19.

Xing J, Sheppard H M, Corneillie S I, Liu X. p53 Stimulates TFIID-TFIIA-promoter complex assembly, and p53-T antigen complex inhibits TATA binding protein-TATA interaction. Mol Cell Biol. 2001 21:3652-61.

Zhao R, Gish K, Murphy M, Yin Y, Notterman D, Hoffman W H, Tom E, Mack D H, Levine A J. Analysis of p53-regulated gene expression patterns using oligonucleotide arrays. Genes Dev. 2000 14:981-93.

Xue W, Zender L, Miething C, Dickins R A, Hernando E, Krizhanovsky V, Cordon-Cardo C, Lowe S W. Senescence and tumour clearance is triggered by p53 restoration in murine liver carcinomas. Nature 2007 445:656-60.

The invention claimed is:

1. A pharmaceutical composition comprising a compound having the following formula

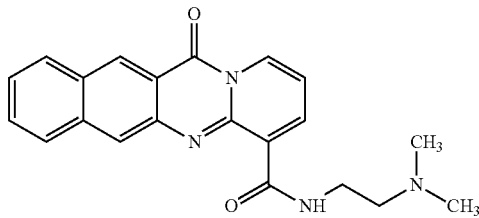

or a pharmaceutically acceptable salt thereof; and a pharmaceutically acceptable carrier.

2. A method of treating cancer, comprising administering to a patient in need thereof a therapeutically effective amount of a compound having the formula

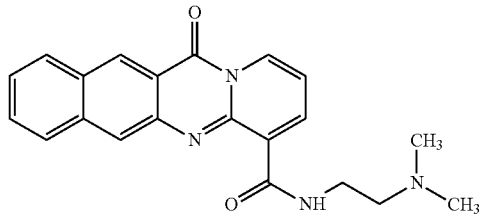 [SMILES: CN(C)CCNC(=O)c1cccn2c(=O)c3cc4ccccc4cc3nc12]

or a pharmaceutically acceptable salt thereof.

3. The method according to claim 2, wherein the compound is administered in a dose in a range of about 0.001 mg/kg to about 200 mg/kg per day.

4. The method according to claim 2, wherein the compound is administered orally, parenterally, subligually, transdermally, rectally, transmucosally, topically, via inhalation, or via buccal administration.

* * * * *